(12) United States Patent
Svendsen

US006916776B2

(10) Patent No.: US 6,916,776 B2
(45) Date of Patent: Jul. 12, 2005

(54) ARTICLE FOR SANITIZING A SURFACE COMPRISING A WIPE CONTAINING AN ADHESIVE, POSITIVELY CHARGED, BINDER

(75) Inventor: Jeffrey S. Svendsen, Plano, TX (US)

(73) Assignee: Svendsen Limited Partnership, Plano, TX (US)

( * ) Notice: Subject to any disclaimer, the term of this patent is extended or adjusted under 35 U.S.C. 154(b) by 38 days.

(21) Appl. No.: 10/945,722

(22) Filed: Sep. 21, 2004

(65) Prior Publication Data

US 2005/0034255 A1 Feb. 17, 2005

Related U.S. Application Data

(63) Continuation of application No. 10/210,994, filed on Aug. 2, 2002, now Pat. No. 6,794,352, which is a continuation-in-part of application No. 09/591,923, filed on Jun. 12, 2000, now abandoned.

(51) Int. Cl.$^7$ ................................................. C11D 1/62
(52) U.S. Cl. ........................ 510/438; 510/234; 510/237; 510/238; 510/245; 510/254; 510/363; 510/365; 510/382; 510/384; 510/391; 510/504
(58) Field of Search ................................. 510/234, 237, 510/238, 245, 254, 363, 365, 382, 384, 391, 504

(56) References Cited

U.S. PATENT DOCUMENTS

| | | | |
|---|---|---|---|
| 4,239,792 A | 12/1980 | Ludwa | |
| 4,401,712 A | 8/1983 | Morrison | |
| 4,601,938 A | 7/1986 | Deacon et al. | |
| 4,666,621 A | 5/1987 | Clark et al. | |
| 4,678,704 A | * 7/1987 | Fellows | 442/121 |
| 4,740,398 A | * 4/1988 | Bouchette | 428/28 |
| 4,753,844 A | 6/1988 | Jones et al. | |
| 4,818,594 A | 4/1989 | Albien et al. | |
| 4,837,079 A | 6/1989 | Quantrille et al. | |
| 4,925,722 A | * 5/1990 | Jeffers et al. | 428/131 |
| 4,946,617 A | 8/1990 | Sheridan et al. | |
| 4,987,632 A | 1/1991 | Rowe et al. | |
| 5,091,102 A | 2/1992 | Sheridan | |
| 5,094,770 A | 3/1992 | Sheridan et al. | |
| 5,141,803 A | * 8/1992 | Pregozen | 442/123 |
| 5,213,588 A | 5/1993 | Wong et al. | |
| 5,700,742 A | 12/1997 | Payne | |
| 5,854,147 A | 12/1998 | Nohr et al. | |
| 5,968,204 A | 10/1999 | Wise | |
| 5,980,922 A | 11/1999 | Mackey et al. | |
| 6,001,381 A | 12/1999 | Gordon et al. | |
| 6,015,816 A | 1/2000 | Kostyniak et al. | |
| 6,113,815 A | 9/2000 | Elfersy et al. | |
| 6,120,587 A | 9/2000 | Elfersy et al. | |
| 6,121,165 A | 9/2000 | Mackey et al. | |
| 6,133,166 A | 10/2000 | Nissing et al. | |
| 6,270,878 B1 | 8/2001 | Wegele et al. | |
| 6,288,076 B1 | 9/2001 | Kostyniak et al. | |
| 6,313,049 B1 | 11/2001 | Heady et al. | |
| 6,322,665 B1 | 11/2001 | Sun et al. | |
| 6,340,663 B1 | 1/2002 | Deleo et al. | |
| 6,376,443 B1 | 4/2002 | Julemont | |
| 6,387,856 B1 | 5/2002 | Ofosu-Asante et al. | |
| 6,395,701 B1 | 5/2002 | Connor et al. | |
| 6,399,560 B1 | 6/2002 | Kwon et al. | |
| 6,429,261 B1 | 8/2002 | Lang et al. | |
| 6,559,189 B2 | 5/2003 | Baker, Jr. et al. | |
| 6,596,657 B1 | 7/2003 | Shalaby | |
| 6,596,681 B1 | 7/2003 | Mahieu et al. | |

(Continued)

FOREIGN PATENT DOCUMENTS

| | | | |
|---|---|---|---|
| EP | 0412131 B1 | | 2/1991 |
| EP | 0778731 B1 | | 6/1997 |
| EP | 0791362 A3 | | 8/1997 |
| EP | 1059032 | * | 12/2000 |
| EP | 1059032 A1 | | 12/2000 |
| EP | 1086648 A1 | | 3/2001 |
| EP | 1167510 A1 | | 1/2002 |
| EP | 1268740 B1 | | 1/2003 |
| WO | 90/05771 | * | 5/1990 |
| WO | WO90/05771 | | 5/1990 |
| WO | WO92/20228 | | 11/1992 |
| WO | WO01/23510 | | 4/2001 |
| WO | WO01/38480 | | 5/2001 |
| WO | WO01/49296 | | 7/2001 |
| WO | WO01/79410 A1 | | 10/2001 |
| WO | WO02/036339 A3 | | 5/2002 |
| WO | WO03/014284 A1 | | 2/2003 |
| WO | WO03/018732 A1 | | 3/2003 |

OTHER PUBLICATIONS

Advertising materials for QUIX PLUS food service towels, Chicopee and BettyMills.com, 2002 and 2004, with Chicopee Finish Formulation for MEF II Line Only, Jun. 15, 1999.

RHOPLEX HA–8 Self–crosslinking Acrylic Emulsion for Textiles, *Textiles and Nonwovens,* Rolm and Haas Company, 1995.

*Primary Examiner*—Charles Boyer
(74) *Attorney, Agent, or Firm*—Steven W. Smith

(57) ABSTRACT

A restaurant cleaning towel made from a substrate such as a woven, nonwoven, or knit fabric. A sanitizer release polymer composition comprising at least one cationic (or alternatively, nonionic) surfactant is bound to the surface of the towel. Preferably, the cationic surfactant is present in the sanitizer release polymer composition in an amount of about 1 to about 10 weight percent, based on a total weight of the composition. The composition may also include at least one nonionic co-surfactant in combination with the cationic surfactant. The towel also includes a color label on its surface to identify the area of the restaurant in which the cleaning towel is to be utilized. The towel may optionally include an international icon, a tactile label, and/or a label in a plurality of languages identifying the area where the towel is to be utilized.

18 Claims, 3 Drawing Sheets

U.S. PATENT DOCUMENTS

| | | |
|---|---|---|
| 6,613,729 B1 | 9/2003 | Cole et al. |
| 6,635,676 B2 | 10/2003 | Baker, Jr. et al. |
| 6,673,761 B2 | 1/2004 | Mitra et al. |
| 2002/0022050 A1 | 2/2002 | Anderson et al. |
| 2002/0031966 A1 | 3/2002 | Tomarchio et al. |
| 2002/0045667 A1 | 4/2002 | Baker, Jr. et al. |
| 2002/0106399 A1 | 8/2002 | Durden |
| 2002/0119207 A1 | 8/2002 | Baker, Jr. et al. |
| 2002/0146950 A1 | 10/2002 | Reich |
| 2002/0183233 A1 | 12/2002 | Mitra et al. |
| 2003/0017194 A1 | 1/2003 | Joerger et al. |
| 2003/0060105 A1 | 3/2003 | Puckhaber et al. |
| 2003/0100465 A1 | 5/2003 | Kilkenny et al. |
| 2003/0109405 A1 | 6/2003 | Kellar et al. |
| 2003/0109411 A1 | 6/2003 | Kilkenny et al. |
| 2003/0148917 A1 | 8/2003 | Mitra et al. |
| 2003/0194932 A1 | 10/2003 | Clark et al. |
| 2003/0199415 A1 | 10/2003 | Mondin |
| 2003/0211794 A1 | 11/2003 | Shalaby |
| 2003/0216273 A1 | 11/2003 | Mitra et al. |
| 2004/0040107 A1 | 3/2004 | Bolkan et al. |
| 2004/0043041 A1 | 3/2004 | Baker, Jr. et al. |
| 2004/0062791 A1 | 4/2004 | Branham et al. |
| 2004/0072489 A1 | 4/2004 | Wild et al. |
| 2004/0106533 A1 | 6/2004 | Mitra et al. |
| 2004/0121682 A1 | 6/2004 | Quincy et al. |
| 2004/0137815 A1 | 7/2004 | Ellis et al. |

\* cited by examiner

ARTICLE FOR SANITIZING A SURFACE COMPRISING A WIPE CONTAINING AN ADHESIVE, POSITIVELY CHARGED, BINDER

RELATED APPLICATIONS

This application is a continuation of U.S. patent application Ser. No. 10/210,994 entitled, Cleaning Towel Having a Color Label and Sanitizer Release Polymer Composition, filed Aug. 2, 2002, now U.S. Pat. No. 6,794,352 which is a continuation-in-part of U.S. patent application Ser. No. 09/591,923 entitled, Method of Ensuring Proper Utilization of Specialized Tools, filed Jun. 12, 2000 now abandoned in the name of Jeffrey S. Svendsen.

BACKGROUND OF THE INVENTION

1. Technical Field of the Invention

This invention relates to cleaning supplies. More particularly, and not by way of limitation, the present invention is directed to a cleaning towel having a color label to identify the area in which the cleaning towel is to be utilized, and a sanitizer release polymer composition that maintains the effectiveness of a cleaning solution.

2. Description of Related Art

For a variety of reasons, it has been difficult for many individuals to easily identify and use the proper tool drawn from a collection of similar tools for use on a specific task. This problem is especially evident in the restaurant industry. A common tool used in the restaurant business is a towel. However, for obvious hygienic reasons, different towels are used for different tasks and different areas within the restaurant. For example, specific towels are used to clean the restrooms, other towels are used for cleaning the dining area, while still other towels are used in the kitchen area. However, to many employees, there is no easy way to differentiate which towel is to be used in which area of the restaurant. Additionally, many employees in the restaurant may not be able to read a label or easily understand which towel should be used in a specific area. The supervisors of these employees, although overseeing the employees, also may not be able to easily identify which towel is being used by the employee. Thus it is difficult for employees, as well as supervisors, to easily identify the proper towel for the proper task in the restaurant.

In various industries, there are numerous examples where labeling and coding techniques have been used to distinguish selected tools for use on specific tasks. For example, in the restaurant industry, labels have been applied to towels or other tools used in the restaurant however, as discussed above, some employees may be illiterate, and other employees, although able to read in one language, are not able to read the language of the labels. In other industries, such as the transportation industry, color-coding has been used to identify various goods. For example, hazardous cargo is sometimes identified by a series of red stripes displayed on the outer surface of a container holding the hazardous cargo. However, although the red stripes may be easy for many employees to identify, some employees are color blind and may not be able to easily recognize the hazardous cargo. In other industries, internationally recognized symbols have been used to convey information about particular products. For example, the familiar "skull and cross bones" has been used to identify poisonous materials. However, for tools such as towels in a restaurant, international symbols may become obscured by grease or dirt. In addition, it may be inconvenient to have to spread out a towel to locate an international symbol each time the towel is going to be used.

Review of current cleaning towels utilized in restaurants reveals no disclosure or suggestion of a cleaning towel that provides a solution to the aforementioned problems. Thus, it would be a distinct advantage to have a cleaning towel that identifies the area of the restaurant where each towel is supposed to be used, even when various employees using the towels may be illiterate, may speak and read different languages, or may be color-blind. It is an object of the present invention to provide such a cleaning towel.

Another problem encountered in restaurants is the control of microbial growth on surfaces such as tables, kitchen counters, and bathroom fixtures. To control microbial growth on a surface, a cleaning solution containing antimicrobials such as sanitizers is applied to the surface with a woven or nonwoven fabric. A sanitizer is a compound that reduces microbial contaminants to safe levels as determined by government Public Health requirements. Currently, the safe level is a 99.999% reduction in the bacterial count.

For the process to be effective, the cleaning solution must maintain a certain concentration of sanitizer. A serious problem occurs when the woven or nonwoven fabric of the cleaning towel dilutes the concentration of sanitizer in the cleaning solution. For example, a nonwoven fabric is repeatedly rinsed in a cleaning solution contained in a bucket, while cleaning the table top surfaces of a restaurant. If the nonwoven fabric is diluting the sanitizer in the cleaning solution, then the table top surfaces are not being disinfected. This can lead to an outbreak of pathogenic enteric bacteria, such as nearly all members of the genus *Salmonella* or *E. coli*. Pathogenic enteric bacteria can cause illness, or worse death.

The two most common sanitizers in cleaning solutions are quaternary ammonium compound (QAC)-based or chlorine-based sanitizers. A QAC is an ion, that is a molecule that carries an electric charge. More specifically, a QAC is a cation, that is an ion that posses a positive charge. A nonionic molecule is an ion that posses a neutral charge. An anion is an ion that posses a negative charge. The charge of a molecule affects that molecule's intermolecular interactions. For example, a cation is attracted to an anion, and a cation repels another cation.

Nonwoven fabrics in common use today with cleaning solutions are made with anionic binders and surfactants. The negative charge of the anionic binders and surfactants utilized in nonwoven fabrics attracts and bonds the cationic QAC-based sanitizer to the fabric thereby diluting and neutralizing the concentration of sanitizer in the cleaning solution. Moreover, woven fabrics comprise many interwoven strands of material, thereby creating a large irregular surface area that captures a large number of cationic QACs during use, thereby diluting the concentration of sanitizer in the cleaning solution. Existing methods to solve this problem are to regularly replace the cleaning solution or regularly replenish the concentration of sanitizer. However, these existing methods are not without limitations.

These existing methods are time consuming and expensive. Regularly monitoring and replacing or replenishing the cleaning solution involves considerable employee time and the expense associated with replacing or replenishing the cleaning solution. Additionally, during busy times in many restaurants, replacement or replenishment of the cleaning solution is often forgotten, resulting in insufficient levels of microbial reduction.

Therefore, a need has arisen for a cleaning towel having a sanitizer release polymer composition that is capable of preventing today's fabrics from bonding to sanitizer. Further, a need has arisen for a towel made from a fabric that does not bond to or neutralize the sanitizer. It is an object of the present invention to provide such a cleaning towel.

SUMMARY OF THE INVENTION

In one aspect, the present invention is directed to a cleaning towel utilized to clean in one of a plurality of areas in a restaurant. The towel includes a substrate with a sanitizer release polymer composition bound thereto. The substrate may be, for example, a woven, nonwoven, or knit fabric, a foam or sponge, or the like. The sanitizer release polymer composition may include at least one cationic surfactant. Preferably, the cationic surfactant is present in the sanitizer release polymer composition in an amount of about 1 to about 10 weight percent, based on a total weight of the sanitizer release polymer composition. The sanitizer release polymer composition may also include at least one nonionic co-surfactant. The towel also includes a color label on the surface of the towel to identify the area of the restaurant in which the cleaning towel is to be utilized. Optionally, the towel may include an international icon, a tactile label, and/or a label in a plurality of languages identifying the area where the towel is to be utilized.

In another aspect, the present invention is directed to a restaurant cleaning towel that includes a substrate which is preferably a nonwoven fabric having a nonwoven surface with a sanitizer release polymer composition bound thereto. In this embodiment, the sanitizer release polymer composition comprises at least one nonionic surfactant. The towel also includes a color label on the surface of the towel to identify the area of the restaurant in which the cleaning towel is to be utilized.

In yet another aspect, the present invention is directed to a restaurant cleaning towel utilized to clean in one of a plurality of areas in a restaurant. The towel includes a substrate with a sanitizer release polymer composition bound to a least a portion of the surface of the substrate. The sanitizer release polymer composition preferably comprises at least one cationic surfactant which may be present in the sanitizer release polymer composition in an amount of about 0.1 to about 99 weight percent, based on a total weight of the sanitizer release polymer composition. The cleaning towel also includes a color label on the surface of the towel to identify the area of the restaurant in which the cleaning towel is to be utilized. The label has a configuration and size that are operable to be readily recognized from a distance by an individual supervising an employee using the towel.

BRIEF DESCRIPTION OF THE DRAWINGS

The invention will be better understood and its numerous objects and advantages will become more apparent to those skilled in the art by reference to the following drawings, in conjunction with the accompanying specification, in which.

DETAILED DESCRIPTION OF EMBODIMENTS

A restaurant cleaning towel for ensuring the proper utilization of cleaning towels, and for maintaining the required concentration of sanitizers is disclosed. In many industries, there are situations where many specialized tools or goods must be used for specific tasks. Many problems arise with employees identifying and understanding which tools should be used for specific tasks. In many instances, these problems are exacerbated by employees who cannot read, do not understand the language in which labels may be written, or are unable to distinguish colors (i.e., color blind).

The restaurant industry is one area where this particular problem is especially acute. One such example can be seen in the utilization of cleaning tools. For example, a towel or rag that is used to clean a restroom should not be used to wipe tables or clean the kitchen. Therefore, to provide a simple method of ensuring that an employee utilizes the proper towel for each particular task, each towel is coded with a plurality of indicators to provide easy identification of the proper tool for the proper task.

Figure 1:
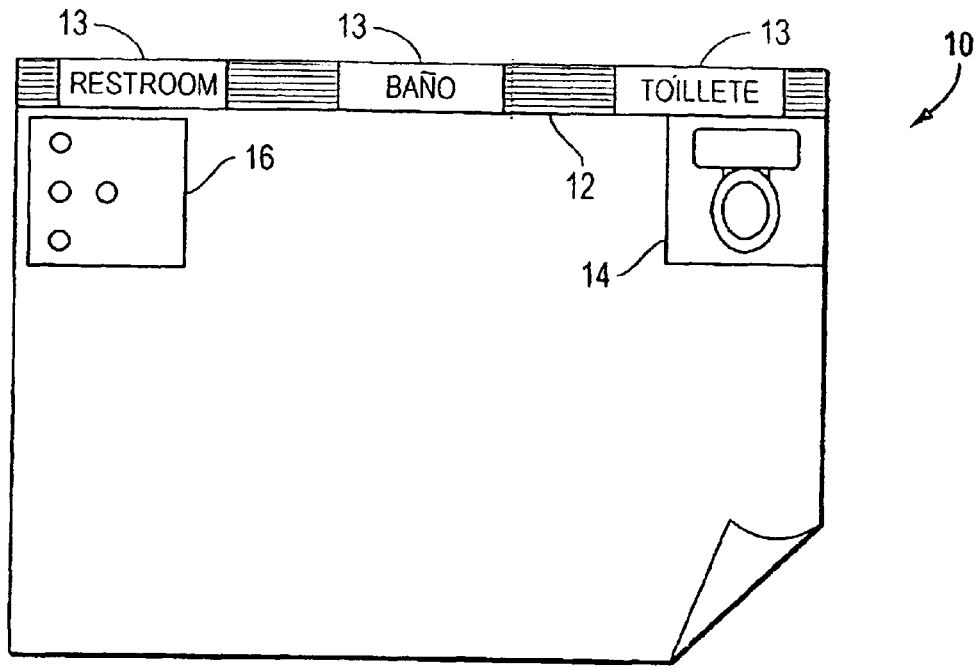
FIG. 1 is a front view of one embodiment of a restaurant cleaning towel for use in a restroom.

FIG. 1 is a front view of a towel 10 for use in a restroom. The towel includes a colored stripe 12 prominently displayed on the towel. For example, in FIG. 1, the stripe is blue to designate that the towel is for use in the restroom and is located on a top border of the towel. Additionally, the towel includes a label 13 having a textual message in several languages, indicating that the towel is to be used for restrooms. The towel also includes an international symbol 14 illustrating a toilet, which also provides an indication that the towel is to be used in the restroom.

Figure 2:
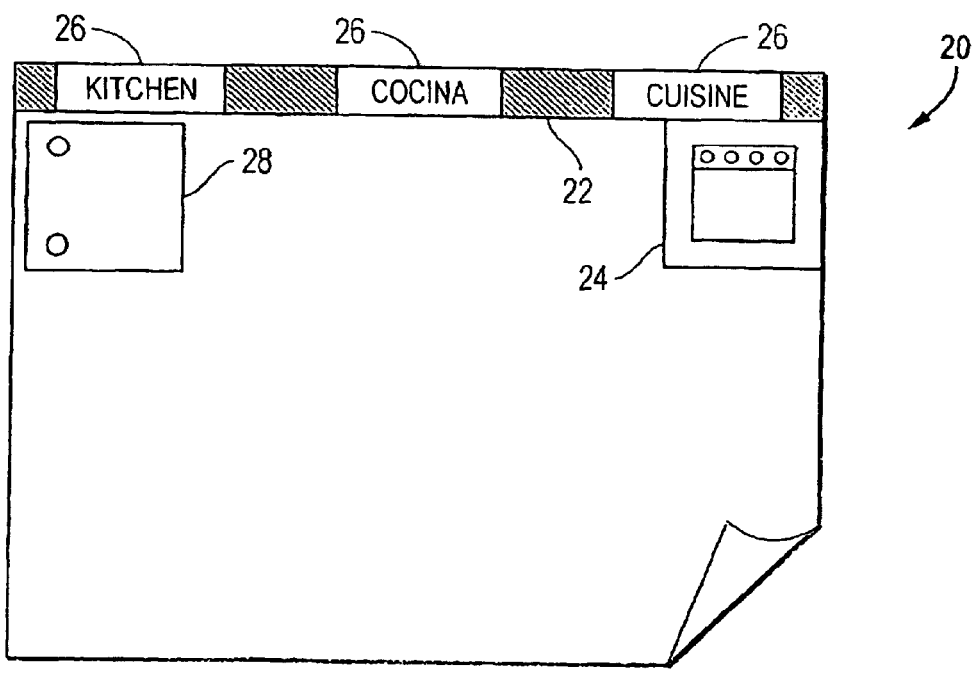
FIG. 2 is a front view of another embodiment of a restaurant cleaning towel for use in a kitchen area of a restaurant.

FIG. 2 is a front view of a towel 20 for use in a kitchen area of a restaurant. The towel includes a colored stripe 22, (green in FIG. 2), an international symbol 24 for a kitchen, and a label 26 indicating that the towel is to be used for the kitchen. In a similar fashion as the towel 10, the towel is labeled in several languages.

Figure 3:
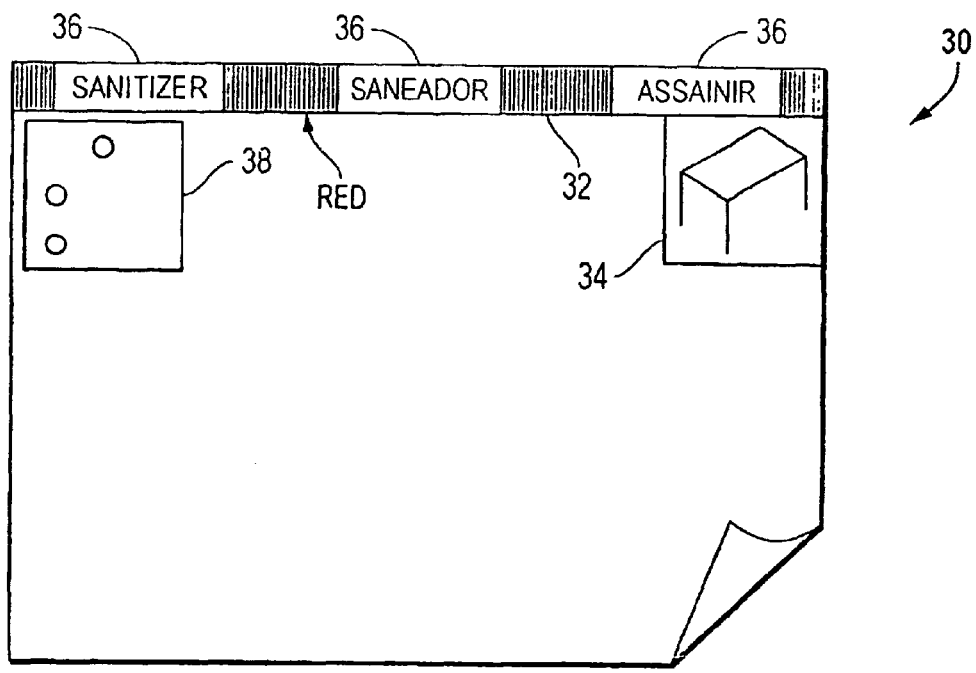
FIG. 3 is a front view of another embodiment of a restaurant cleaning towel for use as a dining room sanitizer.

FIG. 3 is a front view of a towel 30 for use as a dining room sanitizer. The towel may be used to clean tables located within the dining area. The towel includes a colored stripe 32 utilizing the color red for a sanitizer, and an international symbol 34 to indicate that the towel is to be used as a dining room sanitizer. Additionally, a label 36 is also used to indicate, in several languages, that the towel is for use as a dining room sanitizer.

By providing several types of indicators in coding each towel for a specific task, practically any employee can easily and quickly determine which towel is used for each particular task. Since some employees are color blind, a color coding may not be helpful. Thus, labeling in several languages is provided for those employees that are able to read. Additionally, for those employees that cannot read, each towel may also include an international symbol easily understood by most individuals. For example, a symbol of a toilet may be used to indicate a towel is to be used in a restroom.

Figure 4:
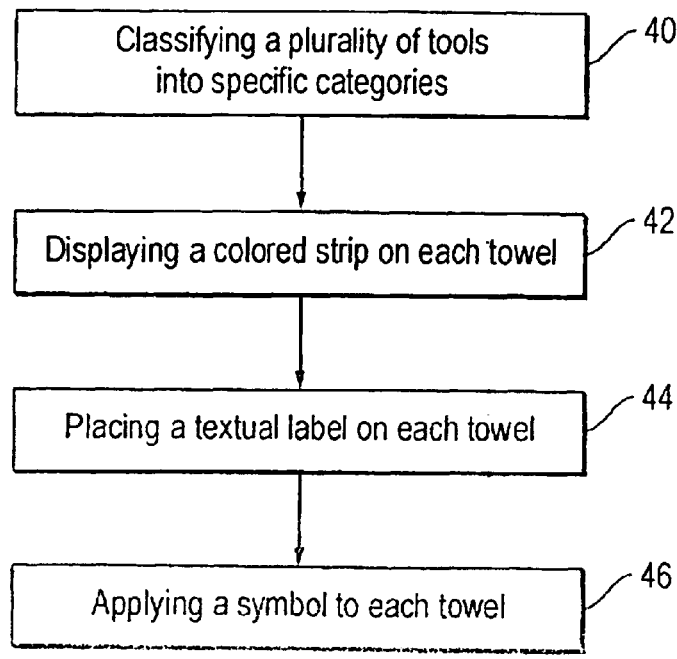
FIG. 4 is a flow chart outlining the steps for ensuring the proper utilization of restaurant cleaning towels or other specialized tools by individuals according to the teachings of the present invention.

FIG. 4 is a flow chart outlining the steps for ensuring the proper utilization of restaurant cleaning towels or other specialized tools by individuals according to the teachings of the present invention. Specifically, FIG. 4 outlines the steps for properly using different towels in specific areas of a restaurant. With reference to FIGS. 1–4, the steps of the method will now be described. Beginning with step 40, a plurality of tools are classified into specific categories. In the example with towels, towels are divided by area and function within the restaurant. Since it is not desired to intermingle the towels from different areas for hygienic reasons, the categories are selected by the location of where the towels are to be utilized. For example, the categories are divided into restroom usage, kitchen usage, and dining room usage.

After determining the different categories for which each towel is to be used, the towels are coded with a plurality of indicators providing easy identification to most individuals utilizing the towels. The method moves from step 40 to step 42 where a colored stripe (12, 22, and 32) is prominently displayed on the towels. The colored stripe of each towel is color coded and associated with a specific category. The color coding provides a readily identifiable label to most people. In the examples described in FIGS. 1–3, the restroom category is blue, the kitchen category is green, and the dining room sanitizer category is red.

Next in step 44, a textual label written in a plurality of languages specifying the category each towel belongs is placed upon each towel. For example, a towel for use in the bathroom would include the word for restroom in several languages, such as English, Spanish, and French. In step 46, a symbol identifying each tool to its associated category is applied to the towel. In the preferred embodiment of the present invention, the symbol is a universally recognizable symbol allowing individuals from any country to understand which category the towel belongs. For example, in the restroom category, a symbol of a toilet may be used. In the kitchen category, a symbol of a stove may be used. The dining room sanitizer may include a symbol of a table to indicate that the towel is used for cleaning within the dining room.

By providing a plurality of indications, all employees can easily identify which towel should be used for each specific task. For those employees who cannot readily identify various colors, other forms of indicators associating the tools to their selected categories are provided. By labeling the tools in several languages, employees who do not understand English are still able to read the label. Additionally, since many employees cannot read, international symbols provide another easily identifiable indication of the specific category the tool should be used for.

There are other possible variations on the coding scheme which may also be used for identifying the proper tool for the desired task. For example, a plurality of indentations in a selected pattern, similar to Braille, may be used to provide the tool with a different tactile feel, and to identify the tool with its specific category. Additionally, numbers, geometric symbols, and icons may also be used to identify the tool. Any coding scheme which provides a plurality of indicators to identify and associate the specific tool to the proper category may be used. For example, referring to FIG. 1, a tactile symbol 16, the Braille "letter R" is disposed on the towel 10 to identify the towel 10 for use in the restroom. Referring to FIG. 2, a tactile symbol 28, the Braille "letter K" is disposed on the towel 20 to identify the towel for use in the kitchen. Referring to FIG. 3, a tactile symbol 38, the Braille "letter S" is disposed on the towel 30 to identify the towel for use with a sanitizer. Each tactile symbol 16, 28, 38 has a different tactile feel to provide a tactile coding scheme that allows blind employees to identify each towel 10, 20, 30, respectively, with its specific category.

In addition to the usage of the coding scheme on towels in the restaurant industry, the method of identifying tools may also be used for various other items. For example, other cleaning tools, such as mops, cleaning containers, trash can liners, dusters, clothing apparel and cleaning supplies may all include coded indicators providing easy identification of the proper tool for the proper task by individuals. Additionally, other tools such as kitchen utensils requiring segregation may be coded. One such example can be seen in the use of knives. Knives used in the preparation of chicken and vegetables should not be interchanged for health reasons.

Also, although the towels use a coding scheme located on the upper portion of each towel, the indicators may be located on other areas of each tool. For example, a mop may include a stitched band located on the mop head. The band may include a colored label, an international symbol, and a textual label in several languages. Additionally, the coding scheme may be set to an industry-wide standard. Thus, specific colors, labels and icons may be consistently used and positioned on tools for a particular industry. This standard coding scheme allows employees jumping from one job to another job at a different location to utilize the proper tool for the proper task while avoiding confusion and additional training.

The disclosed method has been exemplified for the usage of specific tools within a restaurant, however, this method may also be used in other industries. For example, in the medical industry, several tools must be used for specific tasks or specific patients and not used with other tasks or patients. A patient having a contagious disease that requires the use of a specific medical tool may have a coded tool indicating that the tool is only to be used for that specific patient or patients with the same exact ailment, thus preventing the spread of the disease to other patients. As discussed above, the coded tool includes a plurality of indicators allowing the entire medical staff a simple way of identifying the proper tool for the proper task.

Another industry where this method may be particularly useful is within the semiconductor manufacturing industry. During the manufacture of semiconductors, it is imperative that the manufacturing process are main in a sterile environment. Thus the carriage of particles within a "clean room" where the semiconductors are manufactured must be reduced or eliminated. Typically, specialized garments and tools are sterilized prior to use within the clean room. In addition, various areas of the clean room require additional sterilization procedures. It would be advantageous to code various garments, tools, and devices which are allowed to be used within selected areas of the clean room environment with a plurality of indicators identifying the garments, tools, and devices as properly being used within the specified areas of the clean room.

Still another area where the disclosed method can be used is in the safety industry. Various locations within a work area requires the use of a variety of equipment or protective gear. For example, special non-conductive shoes may be required in an area where the production of electricity is present. Therefore, this specific area may be indicated by labeling both the location and the garments with a plurality of indicators, such as colored stripes, labels in a variety of languages, and international symbols to provide easily identifiable indicators to the employees.

Although the method may be used in the industries described above, the method may also be used in other areas not described herein. The disclosed method provides many advantages over existing methods. First, the method provides a simple and easily recognizable indication to various types of people on which specific tools should be used for selected tasks. Additionally, the method may be used by people not normally capable of comprehending the typical coding schemes prevalent in various industries. Additionally, the coding provides indicators which may be readily recognized from a distance. This allows supervisors to identify those individuals that are utilizing the wrong tools for the wrong task, without having to closely watch each employee.

The present invention also provides a substrate with an enhanced sanitizer release polymer composition bound to the surface of the substrate. The substrate may be, for example, a woven, nonwoven, or knit fabric, a foam or sponge, or other structure suitable for absorbing and holding a cleaning solution while wiping off a surface. The enhanced sanitizer release polymer composition may contain at least one cationic surfactant. Optionally, the enhanced sanitizer release polymer composition may contain a co-surfactant. Optionally, the enhanced sanitizer release polymer composition may contain one or more additive agents that functionally and chemically improve the bonding of the cationic surfactant and optional co-surfactant(s) to a particular substrate. Optionally, the enhanced sanitizer release polymer composition may contain one or more fillers. In an alternative embodiment, the enhanced sanitizer release polymer composition contains only nonionic surfactants.

The purpose of any finish, such as a surfactant, is to improve the aesthetic, functional or processing properties of fabrics. Surfactants are a class of materials broadly characterized as being made of molecules containing hydrophilic groups adequately separated from hydrophobic groups. The hydrophobic groups have an affinity for the fiber surface. The hydrophilic groups are attached predominantly to the aqueous medium. Existing fabrics used in the field of sanitizers use anionic surfactants that attract the cationic QAC-based and cationic chlorine-based sanitizers thereby diluting the concentration of sanitizer in the cleaning solution. The enhanced sanitizer release polymer composition of the present invention achieves its unexpectedly superior sanitizer release properties by preferably utilizing a cationic surfactant that repels the cationic QAC-based and cationic chlorine-based sanitizers thereby not diluting the concentration of sanitizer in the cleaning solution. Alternatively, the enhanced sanitizer release polymer composition utilizes a nonionic surfactant that, although not repelling the cationic sanitizers, does not attract the sanitizers like existing anionic surfactants.

As noted above, the enhanced sanitizer release polymer compositions may optionally contain a co-surfactant. Suitable co-surfactants are selected from nonionic, anionic, amphoteric, zwitterionic and semi-polar surfactants. A combination of cationic surfactants and co-surfactants may also be utilized. Preferably, the enhanced sanitizer release polymer compositions are prepared with either cationic surfactants or a combination of cationic and nonionic surfactants.

Suitable cationic surfactants include, for example:
dieicosyldimethyl ammonium chloride;
didocosyldimethyl ammonium chloride;
dioctadecyidimethyl ammonium chloride;
dioctadecyldimethyl ammonium methosulphate;
ditetradecyldimethyl ammonium chloride and naturally occurring mixtures of above fatty groups, e.g. di(hydrogenated tallow)dimethyl ammonium chloride;
di(hydrogenated tallow)dimethyl ammonium methosulphate;
ditallow dimethyl ammonium chloride; and
dioleyidimethyl ammonium chloride.

Suitable cationic surfactants also include imidazolinium compounds, for example, 1-methyl-1-(tallowylamido-)ethyl-2-tallowyl4,5-dihydroimidazolinium methosulphate and 1-methyl-1-(palmitoylamido)ethyl-2-octadecyl 4,5-dihydro-imidazolinium methosulphate. Other useful imidazolinium materials are 2-heptadecyl-1-methyl-1(2-stearoylamido)-ethyl-imidazolinium methosulphate and 2-lauryllhydroxyethyl-1-oleyl-imidazolinium chloride.

Further examples of suitable cationic surfactants include:
dialkyl($C_{12}$–$C_{22}$)dimethylammonium chloride;
alkyl(coconut)dimethylbenzylammonium chloride;
octadecylamine acetate salt;
tetradecylamine acetate salt;
tallow alkylpropylenediamine acetate salt;
octadecyltrimethylammonium chloride;
alkyl(tallow)trimethylammonium chloride;
dodecyltrimethylammonium chloride;
alkyl(coconut)trimethylammonium chloride;
hexadecyltrimethylammonium chloride;
biphenyltrimethylammonium chloride, alkyl(tallow)-imidazoline quaternary salt;
tetradecylmethylbenzylammonium chloride;
octadecyidimethylbenzylammonium chloride;
dioleyidimethylammonium chloride;
polyoxyethylene dodecylmonomethylammonium chloride;
polyoxyethylene alkyl ($C_{12}$–$C_{22}$) benzylammonium chloride;
polyoxyethylene laurylmonomethyl ammonium chloride;
1-hydroxyethyl-2-alkyl(tallow)-imidazoline quaternary salt; and
a silicone cationic surfactant having a siloxane group as a hydrophobic group, a fluorine-containing cationic surfactant having a fluoroalkyl group as a hydrophobic group.

Suitable anionic surfactants include, for example:
from $C_8$ to $C_{20}$ alkylbenzenesulfonates;
from $C_8$ to $C_{20}$ alkanesulfonates;
from $C_8$ to $C_{20}$ alkylsulfates;
from $C_8$ to $C_{20}$ alkylsulfosuccinates; and
from $C_8$ to $C_{20}$ sulfated ethoxylated alkanols.

Suitable nonionic surfactants include, for example, from $C_6$ to $C_{12}$ alkylphenol ethoxylates, from $C_8$ to $C_{20}$ alkanol alkoxylates, and block copolymers of ethylene oxide and propylene oxide. Optionally, the end groups of polyalkylene oxides can be blocked, whereby the free OH groups of the polyalkylene oxides can be etherified, esterified, acetalized and/or aminated. Another modification consists of reacting the free OH groups of the polyalkylene oxides with isocyanates. The nonionic surfactants also include $C_4$ to $C_{18}$ alkyl glucosides as well as the alkoxylated products obtainable therefrom by alkoxylation, particularly those obtainable by reaction of alkyl glucosides with ethylene oxide.

Suitable amphoteric surfactants contain both acidic and basic hydrophilic groups. Amphoteric surfactants are preferably derivatives of secondary and tertiary amines, derivatives of quaternary ammonium, quaternary phosphonium or tertiary sulfonium compounds. The cationic atom in the quaternary compound can be part of a heterocyclic ring. The amphoteric surfactant preferably contains at least one aliphatic group, containing about 3 to about 18 carbon atoms.

At least one cationic surfactant is present in the enhanced sanitizer release polymer composition in an amount of from about 0.1 to about 99 weight percent, preferably from 0.5 to 50 weight percent, more preferably from 1 to 10 weight percent, based on the total weight of the enhanced sanitizer release polymer composition. Preferable surfactants, such as the surfactants discussed above, can be obtained from Chicopee, Inc. of Dayton, N.J., a part of Polymer Group Inc. (PGI)

The composition of the additive agents, such as, for example, crosslinking or curing agents, that functionally and chemically improve the bonding of the cationic surfactant and optional co-surfactant to a particular substrate will depend on the composition and rheology of the substrate.

Figure 5:
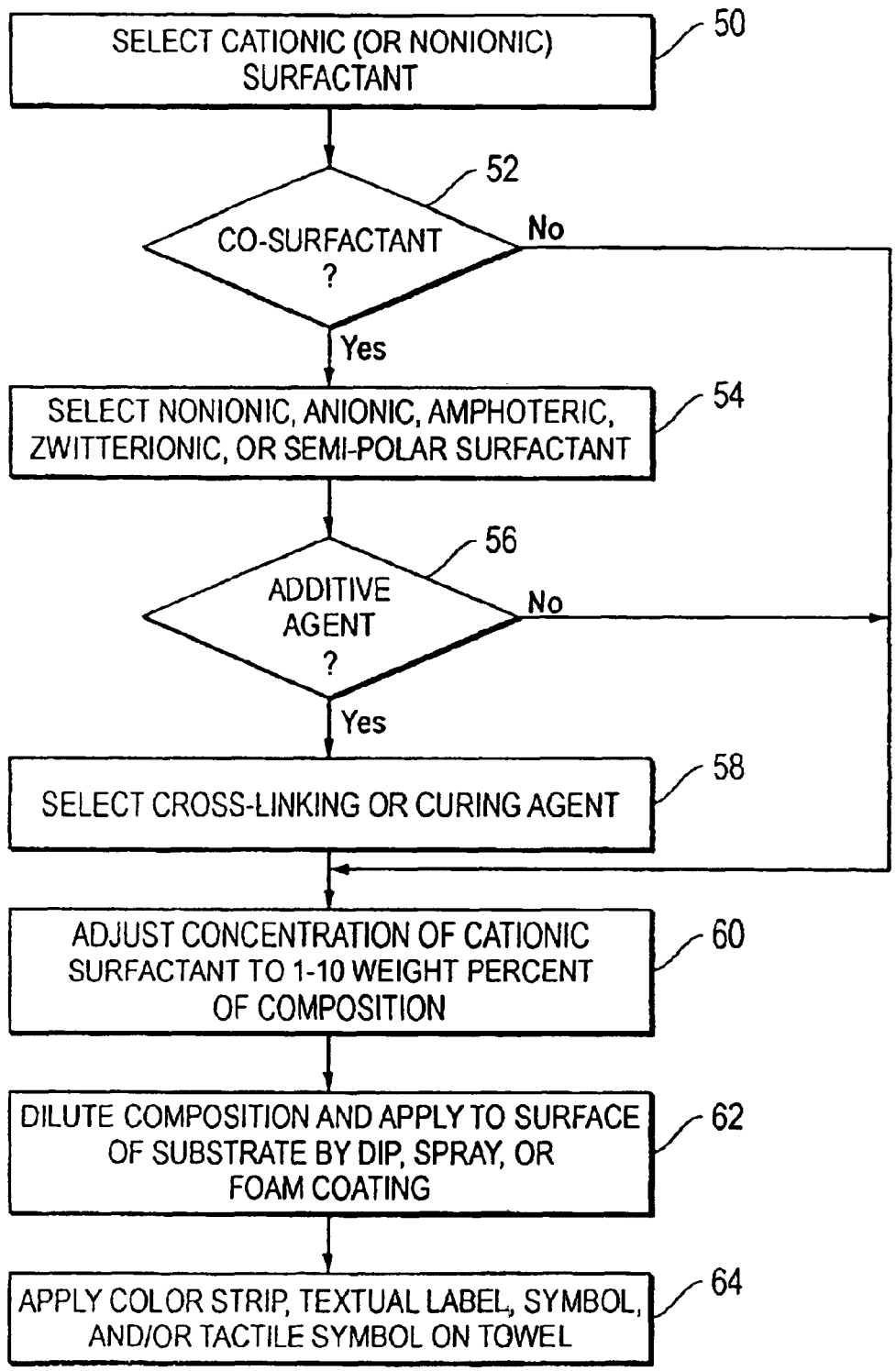
FIG. 5 is a flow chart outlining the steps of a process for manufacturing a restaurant cleaning towel in a preferred embodiment of the present invention.

FIG. 5 is a flow chart outlining the steps of a process for manufacturing a restaurant cleaning towel in a preferred embodiment of the present invention. At step 50, a suitable cationic (or alternatively, a nonionic) surfactant is selected for use in the sanitizer release polymer composition. At step 52, it is determined whether or not a co-surfactant is also to be utilized in the composition. If not, the process moves to step 60. However, if a co-surfactant is to be utilized, the process moves to step 54 where a surfactant is selected from nonionic, anionic, amphoteric, zwitterionic, or semi-polar surfactants. At step 56, it is determined whether or not an additive agent is also to be utilized in the composition. If not, the process moves to step 60. However, if an additive agent is to be utilized, the process moves to step 58 where an additive agent such as, for example, a cross-linking or curing agent is selected.

At step 60, the concentration of the cationic surfactant is preferably adjusted in the composition to a range of 1 to 10 weight percent, based on the total weight of the enhanced sanitizer release polymer composition. At step 62, the enhanced sanitizer release polymer composition is applied to the surface of the substrate. It should be understood by one skilled in the art that the bonding of the enhanced sanitizer release polymer composition to a substrate will depend on the composition and rheology of the substrate. The enhanced sanitizer release polymer composition of the present invention can be applied to the surface of the substrate by any method which is known or unknown. For example, the method may be diluting the enhanced sanitizer release polymer composition with an organic solvent or water, and then applying the solution to the surface of the material to be treated by dip coating, spray coating or foam coating.

At step 64, identifying indicia are applied to the towel to indicate the area of the restaurant where each towel is to be utilized. As indicated above, the indicia may include a color-coded strip, a textual label in a plurality of languages, an international symbol, and/or a tactile symbol such as a Braille letter.

It is thus believed that the operation of the present invention will be apparent from the foregoing description. While the cleaning towel and control method shown and described has been characterized as being preferred, it will be readily apparent that various changes and modifications could be made therein without departing from the scope of the invention as defined in the following claims.

What is claimed is:

1. An article for sanitizing a surface utilizing a sanitizing solution that includes a sanitizer comprising positively charged ions at an effective concentration level, said article comprising:

a substrate that absorbs and holds the sanitizing solution, said substrate having a structure that enables a user to wipe the surface with the substrate, thereby applying the sanitizing solution to the surface;

an adhesive binder that binds together the structure of the substrate, said binder including positively charged ions that provide the substrate with a predominantly positive charge that prevents the substrate from neutralizing the positively charged ions in the sanitizer when the sanitizer is subsequently applied to the substrate, thereby maintaining the concentration level of the sanitizer at the effective level; and a color label on the article to identify to a user, an area in which the article is to be utilized.

2. The article of claim 1 wherein the article is further treated with a cationic surfactant applied to the surface of the substrate.

3. The article of claim 1 wherein the color label has a configuration and size operable to be readily recognized from a distance by an individual supervising the user of the article.

4. The article of claim 1 further comprising an international icon that identifies to the user, the area in which the article is to be utilized.

5. The article of claim 1 further comprising a tactile symbol that identifies to the user, the area in which the article is to be utilized.

6. The article of claim 1 further comprising a textual label printed in a plurality of different languages that identifies to users who speak the different languages, the area in which the article is to be utilized.

7. The article of claim 1 wherein the article is further treated with a nonionic surfactant applied to the surface of the substrate.

8. The article of claim 1 wherein the substrate is a nonwoven fabric comprising a multiplicity of strands of material that are bound together by the adhesive binder.

9. The article of claim 1 wherein the substrate is selected from the group consisting of woven fabrics, nonwoven fabrics, knit fabrics, and foams.

10. The article of claim 1 wherein the article is a sanitizing towel utilized to sanitize one of a plurality of areas in a restaurant.

11. A method of manufacturing a substrate, said substrate being utilized with a sanitizing solution that includes a sanitizer comprising positively charged ions, said method comprising the steps of:

selecting an adhesive binder comprising predominantly positively charged ions;

applying the binder to a plurality of loose strands of material to bind the strands together into a web-like structure forming the substrate, whereby, when the substrate is utilized with the sanitizing solution, the positively charged ions in the binder prevent the substrate from neutralizing the positively charged ions in the sanitizer; and applying a color label on the substrate to identify a use for the substrate.

12. The method of claim 11 further comprising applying a cationic surfactant to the surface of the substrate, said cationic surfactant being selected from the group consisting of:

dieicosyldimethyl ammonium chloride;

didocosyldimethyl ammonium chloride;

dioctadecyldimethyl ammonium chloride;

dioctadecyldimethyl ammonium methosulphate;

ditetradecyldimethyl ammonium chloride and naturally occurring mixtures of fatty groups;

di(hydrogenated tallow) dimethyl ammonium methosulphate;

ditallow dimethyl ammonium chloride; and dioleyldimethyl ammonium chloride.

13. The method of claim 12 wherein the step of applying the cationic surfactant to the surface of the substrate includes the steps of:

mixing a composition in which the cationic surfactant is present in an amount of about 1 to about 10 weight percent, based on a total weight of the composition; and applying the composition to the substrate.

14. The method of claim 13 further comprising the steps of:

selecting a nonionic co-surfactant for use with the cationic surfactant in the composition; and mixing the nonionic co-surfactant with the cationic surfactant to form the composition.

15. A combination for sanitizing a surface, said combination comprising:

a liquid sanitizing solution that includes a sanitizer comprising positively charged ions at an effective concentration level;

a substrate that absorbs and holds the sanitizing solution, said substrate having a structure that enables a user to wipe the surface with the substrate, thereby applying the sanitizing solution to the surface, wherein the structure of the substrate is bound together by an adhesive binder that includes positively charged ions that provide the substrate with a predominantly positive charge that prevents the substrate from neutralizing the positively charged ions in the sanitizer when the sanitizer is subsequently applied to the substrate, thereby maintaining the concentration level of the sanitizer at the effective level; and a color label on the substrate to identify an area in which the substrate is to be utilized.

16. The combination of claim 15 wherein the sanitizer in the sanitizing solution is a quaternary ammonium compound (QAC)-based sanitizer.

17. A combination for sanitizing a surface, said combination comprising:

a liquid sanitizing solution that includes a sanitizer comprising positively charged ions at an effective concentration level;

a cationic substrate that absorbs and holds the sanitizing solution, said substrate having a structure that enables a user to wipe the surface with the substrate, thereby applying the sanitizing solution to the surface, said substrate having a cationic surfactant bonded to the surface of the substrate during manufacturing to provide the substrate with a predominantly positive charge, thereby preventing the substrate from neutralizing the positively charged ions in the sanitizer when the sanitizer is subsequently applied to the substrate; and a color label on the substrate to identify an area in which the substrate is to be utilized.

18. A method of manufacturing an article for sanitizing surfaces, said article being utilized with a sanitizing solution that includes a sanitizer comprising positively charged ions, said method comprising the steps of:

selecting a substrate for the article having a structure suitable for absorbing and holding the sanitizing solution during use;

selecting a cationic surfactant comprising predominantly positively charged ions;

bonding the cationic surfactant to the surface of the substrate to provide the substrate with a predominantly positive charge, whereby, when the article is subsequently utilized with the sanitizing solution, the positively charged substrate prevents the article from neutralizing the positively charged ions in the sanitizer; and applying a color label on the article to identify an area of use for the article.

* * * * *